US009162007B2

(12) United States Patent
Bitis et al.

(10) Patent No.: US 9,162,007 B2
(45) Date of Patent: Oct. 20, 2015

(54) SUPERABSORBENT POLYMER COMPOSITE COMPRISING A SUPERABSORBENT POLYMER AND CELLULOSIC NANOFIBRILS

(75) Inventors: Rozalia Bitis, Kungsbacka (SE); Shabira Abbas, Mölndal (SE); Kent Malmgren, Sundsvall (SE); Mikael Larsson, Mölndal (SE); Anette Larsson, Olofstorp (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 1036 days.

(21) Appl. No.: 13/140,173

(22) PCT Filed: Dec. 17, 2009

(86) PCT No.: PCT/SE2009/051446
§ 371 (c)(1),
(2), (4) Date: Aug. 26, 2011

(87) PCT Pub. No.: WO2010/071584
PCT Pub. Date: Jun. 24, 2010

(65) Prior Publication Data
US 2011/0301027 A1 Dec. 8, 2011

(30) Foreign Application Priority Data
Dec. 19, 2008 (WO) ................. PCT/SE2008/051542

(51) Int. Cl.
*B01J 20/24* (2006.01)
*B01J 20/26* (2006.01)
*B01J 20/22* (2006.01)
*B01J 20/28* (2006.01)
*A61L 15/60* (2006.01)
*A61L 15/28* (2006.01)

(52) U.S. Cl.
CPC ................. *A61L 15/60* (2013.01); *A61L 15/28* (2013.01); *A61L 2400/12* (2013.01)

(58) Field of Classification Search
None
See application file for complete search history.

(56) References Cited

U.S. PATENT DOCUMENTS

| 3,598,742 A | 8/1971 | Jamison et al. |
| 5,350,370 A | 9/1994 | Jackson et al. |

(Continued)

FOREIGN PATENT DOCUMENTS

| DE | 20 2005 020 566 | 4/2006 | |
| DE | 202008007008 U1 * | 9/2008 | ............... D04H 1/54 |

(Continued)

OTHER PUBLICATIONS

"Starch." Encyclopaedia Britannica, Inc., (c)2014. Viewed Sep. 8, 2014 at http://www.britannica.com/EBchecked/topic/563582/starch.*

(Continued)

*Primary Examiner* — Stanley Silverman
*Assistant Examiner* — Daniel Berns
(74) *Attorney, Agent, or Firm* — Drinker Biddle & Reath LLP

(57) ABSTRACT

A superabsorbent polymer composite including superabsorbent polymers and cellulosic nanofibrils having a diameter equal to or less than 100 nm. The composite may be in the form of particles or a foam. Methods for producing the composite and absorbent articles including the superabsorbent polymer composite are also provided.

28 Claims, 7 Drawing Sheets

(56) References Cited

U.S. PATENT DOCUMENTS

| | | | |
|---|---|---|---|
| 5,506,035 A | 4/1996 | Van Phan et al. | |
| 6,046,377 A | 4/2000 | Huntoon et al. | |
| 6,162,541 A | 12/2000 | Chou et al. | |
| 6,540,853 B1 | 4/2003 | Suzuki et al. | |
| 8,343,612 B2 * | 1/2013 | Soder et al. | 428/172 |
| 2003/0111163 A1 | 6/2003 | Ko et al. | |
| 2003/0111774 A1 | 6/2003 | Kellenberger et al. | |
| 2006/0160452 A1 | 7/2006 | Mirle et al. | |
| 2008/0082067 A1 | 4/2008 | Weerawarna et al. | |
| 2010/0221972 A1 * | 9/2010 | Soane | 442/327 |

FOREIGN PATENT DOCUMENTS

| | | |
|---|---|---|
| EP | 0 598 833 | 10/1997 |
| EP | 0 947 549 | 10/1999 |
| EP | 1 207 914 | 8/2003 |
| WO | 99/58091 | 11/1999 |
| WO | 2006/049664 | 5/2006 |
| WO | 2008/113021 | 9/2008 |
| WO | 2009/069641 | 6/2009 |

OTHER PUBLICATIONS

Esp@cenet patent family list for DE202008007008U1. Viewed on Jun. 3, 2015 at http://worldwide.espacenet.com/publicationDetails/inpadocPatentFamily?CC=US&NR=2009324893A1&KC=A1&FT=D&ND=3&date=20091231&DB=EPODOC&locale=en_EP.*

* cited by examiner

SUPERABSORBENT POLYMER COMPOSITE COMPRISING A SUPERABSORBENT POLYMER AND CELLULOSIC NANOFIBRILS

CROSS-REFERENCE TO PRIOR APPLICATION

This application is a §371 National Stage Application of PCT International Application No. PCT/SE2009/051446 filed Dec. 17, 2009, which claims priority to PCT/SE2008/051446 filed Dec. 19, 2008.

FIELD-OF THE INVENTION

The present disclosure relates to a superabsorbent polymer composite including a superabsorbent polymer and cellulosic nanofibrils. The disclosure further refers to a method of producing the superabsorbent polymer composite and an absorbent article including the superabsorbent polymer composite.

BACKGROUND

Advances in absorbent article technology have stimulated the search for absorbent (often superabsorbent) materials with desirable properties such as high absorption, high storage capacity and high gel and mechanical strength.

The absorbent materials may include two or more layers such as liquid acquisition layers, storage layers and distribution layers.

In order to obtain good liquid acquisition capacity it is important that the absorbent material has a high momentaneous liquid acquisition capacity. Open, bulky structures with large capillaries have a high momentaneous liquid acquisition capacity and examples of such materials are cellulosic fluff pulp of thermomechanic or chemithermomechanic (CTMP) type, chemically stiffened cellulosic fibres fibers, waddings of synthetic fibers and porous foam materials.

In order to obtain a good liquid storage capacity it is common that the absorbent structure contains superabsorbent materials. Superabsorbent materials are crosslinked polymers with the capacity to absorb liquid many times their own weight. Organic materials suitable for use as a superabsorbent material can include natural materials such as polysaccharides (particularly modified polysaccharides such as CMC: carboxymethylcellulose), polypeptides and the like, as well as synthetic materials such as synthetic hydrogel polymers. Such hydrogel polymers include, for example, polyacrylates (particularly alkali metal salts of polyacrylic acids), polyacrylamides, polyvinyl alcohol, polyacrylamides, polyvinyl pyridines, and the like. Other suitable polymers include polyvinylamine, hydrolyzed acrylonitrile grafted starch, acrylic acid grafted starch, and isobutylene maleic anhydride copolymers and mixtures thereof. The absorption mechanism of such superabsorbents is thought to be based on the fact that the polymer chain contains a plurality of charged groups, which make it possible for the polymer network to absorb aqueous liquids by means of osmotic forces.

The superabsorbent material in an absorbent structure, i.e. a diaper core, is often in the form of small particles, which are arranged and contained in a fibrous matrix. The fibrous matrix usually includes cellulosic fluff pulp of thermomechanic, chemical or chemithermomechanical type, but a certain amount of synthetic fibers are also common.

One problem with absorbent structures containing superabsorbent material is that it is difficult to distribute and maintain the superabsorbent material in the desired location in the absorbent structure, both during storage and during use of the article. Another problem with absorbent structures containing superabsorbent material is so-called gel blocking. This problem occurs by the fact that the liquid-containing superabsorbent particles swell and form a gel. The gel blocks the liquid transport and gives rise to an accumulation of liquid in certain portions of the absorbent structure while other portions of the structure become more-or-less non-utilized.

In order to obtain a superabsorbent material with high mechanical strength, the degree of crosslinking of the polymer is crucial. The more crosslinking in a polymeric structure, the more the mechanical strength increases. However, a high degree of crosslinking within a structure restricts the swelling capacity of the material, and highly-crosslinked superabsorbent materials are brittle and break easily. The performance of superabsorbent materials in different applications is highly dependent on the elastic modulus, the resistance to fracture and the water absorbance capacity among other properties. These properties are strongly affected by the degree of crosslinking. It has been shown that for polyacrylic acid (PAA) the equilibrium degree of swelling decreases and the elastic modulus increases with an increasing degree of crosslinking, as expected from theory.

Absorbent web composites including a superabsorbent polymer component and fibrous material, such as cellulose fibers and processes for their production are known.

An example of this type of material is described in US 2003/0111163, which describes a process for making an absorbent fibrous web composite including a stable and controllable dispersion of superabsorbent polymer. Two polymer precursors, for example, acrylic acid or methacrylic acid, are added in separate stages to form a superabsorbing polymer on or in a pre-formed fibrous web, which includes a plurality of hydrophilic fibers, e.g. microfibrillar cellulose or microcrystalline cellulose.

Similarly, US 2003/0111774 describes a process for making an absorbent fibrous composite nonwoven web including e.g. superabsorbent polymers and plurality of hydrophilic fibers. The polymerization of the superabsorbent polymer is integrated into the process of forming the absorbent composite nonwoven web.

EP 1 207 914 further discloses an absorbent structure including an open-cell foam structure wherein the pore walls of the structure include a liquid-storing material, e.g. polyacrylate. The absorbent structure is characterized in that the pores of the foam structure contain hydrophilic fibers, e.g. cellulose fibers, at which at least the main part of the hydrophilic fibers are firmly anchored in the pore walls of the foam structure, and that the fiber amount is at least 10% by weight of the total weight of the open-cell foam in dry condition.

Foam materials made of traditional superabsorbent polymers (e.g. polyacrylic acid/polyacrylate polymers) are usually hard and stiff when dry, and inelastic when wet—they tend to fall apart under pressure. For these reasons, superabsorbent materials are usually included in absorbent articles in granular form.

It would therefore be advantageous to design a new absorbent material including superabsorbent polymers and cellulosic fibers with improved mechanical and gel properties in a swollen condition, and at the same time retain absorbent, spreading and storage properties. In particular, it would be useful to provide an absorbent material which has improved strength, yet which—at the same time—does not suffer from lack of flexibility and brittleness.

SUMMARY

A first aspect relates to a superabsorbent polymer composite including a superabsorbent polymer and cellulosic fibrils. The cellulosic fibrils are nanofibrils having a diameter equal to or less than 100 nm.

Suitably, the composite does not contain cellulosic fibers having an average diameter greater than 100 µm.

The superabsorbent polymer composite may further include cellulosic microfibers having a diameter greater than 100 nm but less than or equal to 100 µm, preferably a diameter greater than 100 nm but less than or equal to 10 µm.

Suitably, the superabsorbent polymer composite has a nanofibril content of 0.1-20 wt % of the superabsorbent polymer, preferably 0.5-15 wt %, and more preferably 0.5-5 wt %. Additionally, the composite may have a microfiber content of 0.1-20 wt % of the superabsorbent polymer and preferably 0.5-15 wt %.

The superabsorbent polymer may include a repeating unit derived from the group consisting of acrylic acid and its salts, methacrylic acids and its salts and combinations thereof.

The superabsorbent polymer composite may include an organic cross-linker. The organic cross-linker content may be 0.1-20 wt % of the superabsorbent polymer, preferably 0.5-15 wt %, and more preferably 0.5-5 wt %.

The composite may be in the form of particles or a foam. If in the form of a foam, the nanofibrils may be incorporated into the pore walls of the foam. The foam may have a pore size gradient. Additionally, the foam may include one or more substances selected from the group consisting of plasticizers, surfactants and blowing agents.

A second aspect relates to an absorbent article having an absorbent structure including the superabsorbent polymer composite. The absorbent article may be a diaper, a pant diaper, an incontinence guard, a sanitary napkin or the like and of the kind including a liquid pervious topsheet, a liquid impervious backsheet, said absorbent structure arranged therebetween.

A third aspect relates to a method for making a superabsorbent polymer composite, said method including the steps of:
a. providing cellulosic nanofibrils having a diameter equal to or less than 100 nm suspended in a solvent,
b. optionally, adding microfibers having a diameter greater than 100 nm but less than or equal to 100 µm suspended in a solvent,
c. adding one or more monomers,
d. adding a neutralizer,
e. adding a crosslinker,
f. adding an initiator, and
h. polymerizing the monomers and crosslinker to form a superabsorbent polymer composite including superabsorbent polymers, cellulosic nanofibrils and optionally microfibers.

The steps a), b), c), d), e) and f) can take place in any order.

The initiator may be selected from the group consisting of oxidizing initiators, azo initiators, photoinitiators and thermal initators, and combinations thereof.

If particles are to be formed, the above method may further include the step of (i) forming the composite into particles. If a foam is to be formed, the above method may further include the step of (g) forming the composite into a foam. The step (g) takes place after steps (a)-(f), but before step (h) of the above method.

The method for making the foam may further include the steps of adding one or more substances selected from the group consisting of plasticizers, surfactants and blowing agents. An additional step may be to add a viscosity control agent.

A fourth aspect relates to a method for making an absorbent structure, said method including carrying out the method set out above, and incorporating the resulting superabsorbent polymer composite, foam or particles into said absorbent structure.

A fifth aspect relates to a method of using the cellulosic nanofibrils for increasing the gel strength of a superabsorbent polymer.

Definitions

The term "nanofibrils" means individual fibrils having a diameter equal to or less than 100 nm at all points along the nanofibril. The diameter may vary along its length. The nanofibrils may exist as individual fibers and/or as clusters of nanofibrils. The term "nanofibrillated cellulose (NFC)" is used interchangeably with the term "nanofibrils".

The term "microfibers" means individual fibers having a diameter greater than 100 nm but less than or equal to 100 µm at all points along the microfiber. More specifically, the microfibers may have a diameter greater than 100 nm but less than or equal to 10 µm or a diameter greater than 100 nm but less than or equal to 1 µm. The diameter may vary along its length. The microfibers may exist as individual microfibers and/or as clusters of microfibers in the composite. The term MFC (microfibrillated cellulose) is used interchangeably with the term "microfibers".

The term "cellulosic" refers to fibrils or fibers from natural sources such as woody and non-woody plants, regenerated cellulose and the derivatives from these fibers by means of chemical, mechanical, thermal treatment or any combination of these. Further, "cellulosic" also refers to cellulosic or cellulose-containing fibers produced by microorganisms.

The term "porous" is used herein to describe a material that has pores and, which admits the passage of gas or liquid through these pores.

The term "superabsorbent polymer composite" (also called herein simply "composite") means a structure made up of at least two distinct components: superabsorbent polymer and cellulosic fibrils. These components remain separate and distinct on a microscopic level in the composite. Other components may also be present in the composite.

The term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

"Superabsorbent polymers" are water-swellable, water-insoluble organic or inorganic materials capable of absorbing at least about 20 times their own weight in an aqueous solution containing 0.9 weight percent (wt %) of sodium chloride. Organic materials suitable for use as a superabsorbent material can include natural materials such as polysaccharides (including modified polysaccharides such as CMC: carboxymethyl cellulose), polypeptides and the like, as well as synthetic materials such as synthetic hydrogel polymers. Such hydrogel polymers include, for example, alkali metal salts of polyacrylic acids (pAA), polyacrylamides, polyvinyl alcohol, polyacrylates, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers can be preferably lightly crosslinked to render the material substantially water insoluble. Particular superabsorbent materials may be further surface crosslinked so that the outer surface or shell of the superabsorbent particle, fiber, flake, sphere, etc. possesses a higher crosslink density than the inner portion of the superabsorbent.

The term "absorption under load (AUL)" denotes a method used herein to measure the absorption under load of a superabsorbent polymer composite in the form of particles or foam in an aqueous solution of 0.9% NaCl or defibrinated sheep blood.

The term "crosslinked" is used herein to describe a material in which particles or regions of a first component of the material are interlinked by means of a second component. Generally, covalent chemical bonds are formed between the first and second components. Increased crosslinking in a material provides it with increased strength and increased stiffness (and hence lower flexibility).

The term "particles" includes the composite in the form of for example powder, granules, flakes, spheres, and the like.

The term "foam" is used herein to describe one form of the composite wherein the composite includes gas bubbles. Foams are materials that are formed by trapping gas bubbles in a liquid or solid. Solid foams form an important class of lightweight cellular materials. Foams can be classified into two types based on their pore structure. The first type of foam is called an open-cell foam. These foams contain pores that are connected to each other and form an interconnected network. The second type of foams does not have interconnected pores, and are called closed-cell foams.

A "surfactant" is a component, which, when present in small amounts, facilitates the formation of a foam, or enhances its colloidal stability by inhibiting the coalescence of bubbles.

A "blowing agent" is a substance which is capable of producing a cellular structure in a variety of materials that undergo hardening or phase transition (such as polymers, plastics, metals). They are applied when the blown material is in liquid stage.

The term "absorbent article" includes diapers, incontinence guards, sanitary napkins, wound dressings, bed protectors and the like.

The term "defibrinated sheep blood" includes sheep blood from which substantially all fibrin has been removed. Sufficient fibrin has been removed so that coagulation of the blood is avoided during storage for at least two weeks.

The term "z-direction" is used herein as the direction being generally out of plane as compared to the generally planar configuration of an absorbent structure, i.e., through the thickness of the absorbent structure.

BRIEF DESCRIPTION OF THE DRAWINGS

Embodiments of the invention will now be described in more detail with reference to the enclosed Figures, in which.

DETAILED DESCRIPTION OF PREFERRED EMBODIMENTS

Superabsorbent Polymer Composite

Figure 1:
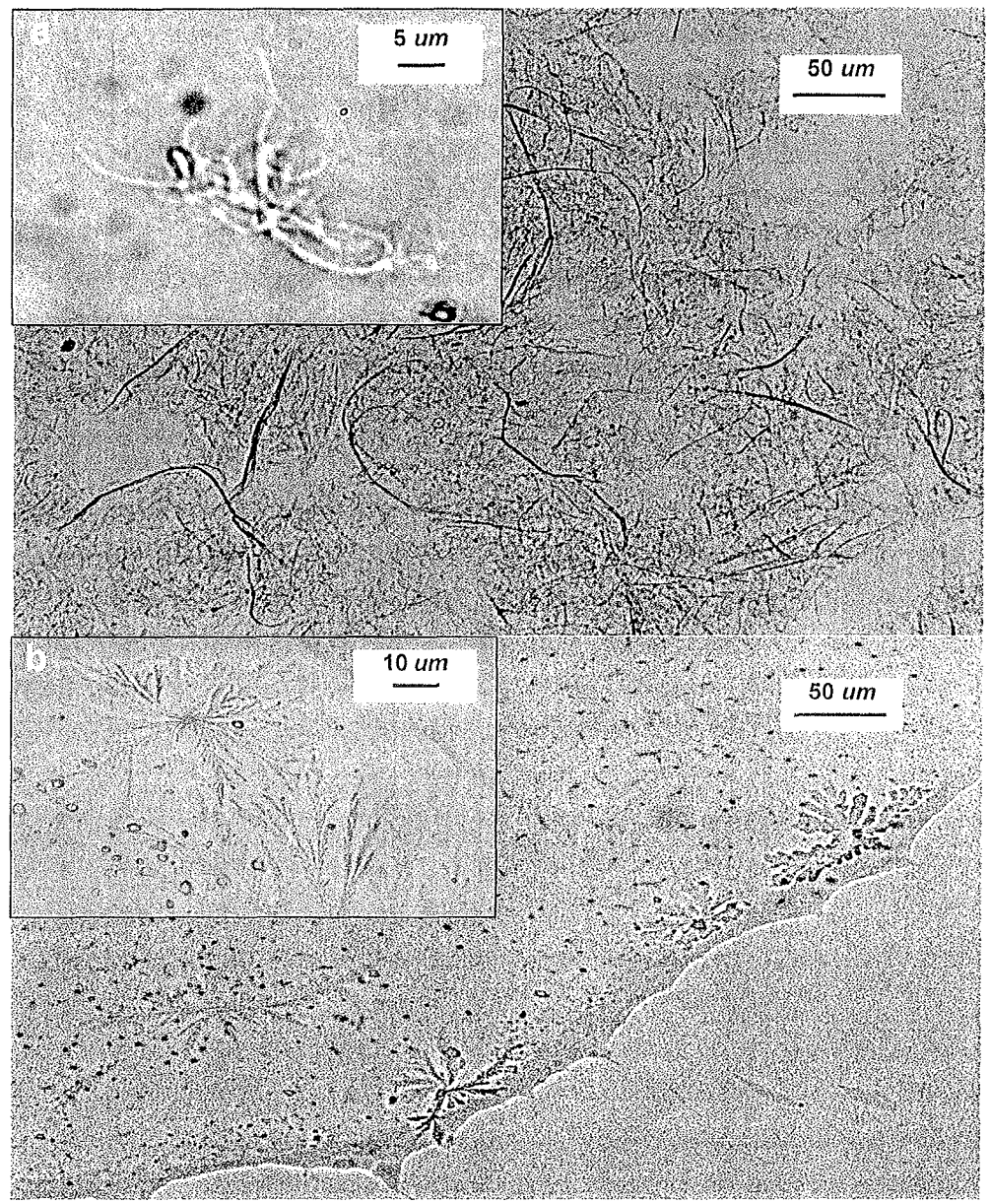
FIG. 1 shows optical microscopy images of a suspension of nanofibirillated (NFC) and microfibrillated (MFC) cellulose. (a) Image of wet 2× diluted suspension using a 10× objective. The scale line in Figure 1a corresponds to 50 µm. Insert is 25× diluted using a 100× objective. The scale line in the insert in FIG. 1a corresponds to 5 µm. (b) Image of filtered and dried suspension using a 10× objective. Insert is captured using a 50× objective. The scale line in FIG. 1b corresponds to 50 µm, while the scale line in the insert in FIG. 1b corresponds to 10 µm.

The present disclosure provides a superabsorbent polymer composite of certain materials. The composite includes two main components: superabsorbent polymers, and cellulosic fibrils that are nanofibrils. The nanofibrils have a diameter equal to or less than 100 nm.

Suitable superabsorbent polymers can include natural materials such as polysaccharides (including modified polysaccharides such as CMC: carboxymethyl cellulose), polypeptides and the like. Other suitable polymers include hydrolyzed acrylonitrile grafted starch, acrylic acid grafted starch, and isobutylene maleic anhydride copolymers and mixtures thereof The SAP can be CMC.

Synthetic materials can also be used as superabsorbent polymers. In particular, superabsorbent polymer including repeating units derived from the group consisting of acrylic acid (AA) monomers and its salts, methacrylic acids and its salts and combinations thereof can be used. Acrylonitrile, acryloylchloride, acrylic esters (e.g. tert-butyl- or methylacrylic acid ester), unsaturated lactones, anhydrides, acrylamide monomers, secondary or tertiary acrylamides, or other alkenes, monomers having at least one alkene (olefin) group and at least one sulfonate or sulfonic acid group, ethylene sulfonate esters, ethylene sulfonic halides and heterocyclic monomers containing sulphonamide linkages are suitable monomers. Combination of these monomers with each other, and with other monomers, is possible when forming the polymers. Other superabsorbent polymers may be polymeric sulfonic acids such as styrene sulfonic acid, sodium styrene sulfonate and/or similar compounds. If neutral monomers are used, these should be hydrolyzed in order to achieve a charged polymer.

Hydrolysis of polyacrylamide gels to polyacrylic acid gels may be carried out using aqueous acidic solution, see G. Smets, A. M. Hesbain, J. Polymer Science, Vol. 11, p. 217-226 (1959).

The acidic monomers of the superabsorbent polymers need to be neutralized in order to increase their osmotic pressure. Suitable neutralizers include lithium hydroxide, sodium hydroxide, potassium hydroxide, lithium carbonate, sodium carbonate, potassium carbonate, lithium bicarbonate, sodium bicarbonate, potassium bicarbonate, and ammonia. The carboxylic acid group of the acidic monomer can be partially neutralized into lithium, sodium, potassium, or ammonium salt, or the mixtures of two or more thereof. The degree of neutralization of the acid group is 10-95%, preferably 30-80%, and more preferably 55-75%.

The superabsorbent polymer composite may include an organic cross-linker. The superabsorbent polymer composite may have an organic cross-linker content of 0.1-20 wt % of the superabsorbent polymer, preferably 0.5-15 wt %, and more preferably 0.5-5 wt %. Organic cross-linking agents may have more than one (e.g. 2) functional groups which can be incorporated into a growing polymer in the polymerisation reaction. They act to bridge polymer chains, providing strength to the resultant gel. Known cross-linking agents are e.g. triallylisocyanurate, triallylcyanurate, N,N'-bisacrylylcystamine, N,N'-diallyltartardiamide, 1,3-diacryloylethyleneurea, ethylenediacrylate, N,N'-methylenebisacrylamide (MBA), N,N'-propylenebisacrylamide, di(acrylamindemethyl)-ether, N,N'-dimethylol(methylenebis(acrylamide)), 1,2-diacrylamide ethyleneglycol and 1,3-diacryloylethyleneurea.

Other crosslinking agents can cross-link polymers after their formation. Examples of these are formaldehyde, methylolated nitrogen compounds such as dimethylolurea, dimethylolethyleneurea and dimethylolimidazolidone, dicarboxylic acids for example maleic acid, dialdehydes such as glyoxal, diepoxides, diisocyanates, divinyl compounds such as divinyl sulfone, dihalogen containing compounds such as dichloroacetone and 1,3-dichloropropan-2-ol, halohydrins such as epichlorohydrin, bis(epoxypropyl)ether, dichloroethane, divinylsulfone, epichlorohydrin, ethylene glycol-bis(epoxypropyl)ether, vinylcyclohexene dioxide, 1,3-dichloro-2-propanol, 1,3-bis([3-hydroxy-1-chloropropoxy)-2-propanol, 1,3-bis($\beta$-hydroxy-1-chloropropoxy)ethane, 1,2:3,4-diepoxybutane, 1,2:5,6-diepoxyhexane, 2,3-dibromo-1-propanol, 2,3-dichloro-1-propanol, 2,2-dichloroethyl ether, methylenebis(acrylamide), trisacrylolhexahydrotriazine, acrylamidomethylene chloro-acetamide, 2,4,6-trichloropyrimidine, 2,4,5,6-tetrachloropyrimidine, cyanuric chloride, triallyl cyanurate, dichloroacetic acid and phosphorous oxychloride.

Individual nanofibrils and/or clusters of nanofibrils fully separated from the cellulose fiber can be used. The individual nanofibrils typically have a diameter equal to or below 100 nm at all points along the nanofibril. The diameter may vary along its length. Further, the length of the nanofibrils should not be too short in order to give the composite the desired effect. In particular embodiments, the nanofibrils have a length greater than 1 µm.

The presence of nanofibrils (NFC) in the composite is crucial to obtain the improved mechanical strength as well as good absorbing, liquid spreading, and liquid storage properties. The nanofibrils stabilize the polymer network of the superabsorbent polymer composite and do not interfere with the absorption. Because of the improved gel strength, a high degree of crosslinking is not necessary. This fact also diminishes the risk for gel blocking. These properties give better controlled swelling and this can be utilized in designing an absorbent structure. Without wishing to be bound by theory, it may be that the nanofibrils act as crosslinking agents, but without forming strong chemical bonds within the composite. The composite therefore gains strength, but is more flexible in terms of expansion, so thus does not become so brittle. The flexibility of the composite in turn allows the composite to expand more freely and absorb more liquid.

A particular wt % of nanofibrils compared to the amount of superabsorbent monomer in the superabsorbent polymer composite lies within the range of 0.1-20 wt %, preferably 0.5-15 wt %, and more preferably 0.5-5 wt %.

Further, as well as nanofibrils and superabsorbent polymers, the superabsorbent polymer composite can also include microfibers (MFC), in order to adjust the absorption capacity of the composite. For example, by adding microfibers in addition to nanofibrils a sample with higher liquid distributing capacity can be created.

Microfibers, herein, mean individual microfibers and/or clusters of microfibers fully separated from the cellulose fiber. Suitable diameters for the cellulosic microfibers are greater than 100 nm but less than or equal to 100 µm, and preferably greater than 100 nm but less than or equal to 10 µm. It is possible that the diameter varies along its length.

A particular wt % of microfiber compared to the amount of superabsorbent monomer in the superabsorbent polymer composite lies within the range of 0.1-20 wt % and preferably 0.5-15 wt %.

The composite may include nanofibrils and microfibers. Particular wt % of microfibers compared to superabsorbent monomer lies within the range of 0.1-20 wt % and preferably 0.5-15 wt %, and the particular wt % of nanofibrils compared to superabsorbent monomer lies within the range of 0.1-20 wt % and preferably 0.5-15 wt %.

Suitably, the composite does not contain cellulosic fibers having an average diameter greater than 100 µm.

The superabsorbent polymer composites optionally include a plasticizer. By plasticizing agent/plasticizer is meant a chemical substance that is used together with a polymeric material to change its mechanical properties from hard and stiff to soft and flexible. Plasticizing agent/plasticizers embed themselves in between the polymer chains, spacing them apart thereby increasing the free volume, and thus significantly lowering the glass transition temperature of the polymer and making it softer.

Plasticizing agents selected for use possess a range of properties. Generally, the plasticizing agents can be liquid or a solid and have a range of molecular weights and architectures and are compatible with the superabsorbent polymer composite. They could be low molecular weights substances or polymers and are non-volatile and non-reactive. Generally, liquid plasticizing agents are chosen to be miscible with the monomers which are used in the polymerization. Typically, low molecular weight plasticizing agents are derived from low molecular weight acids or alcohols; examples are glycerol and citric acid. The low molecular weight acids or alcohols could also be esterified with respectively a monofunctional alcohol or monofunctional acid. Examples of such plasticizing agents are esters of mono- and multibasic acids, such as isopropyl myristate, dibutyl phthalate, diisoctyl phthalate, dibutyl adipate, dibutylsebacate and the like. Typically polymeric plasticizing agents include polyalkylene oxides having weight average molecular weights of about 150 to about 1500, such as polyethylene oxides, polypropylene oxides, polyethylene glycols and copolymers thereof.

Water will act as a plasticizing agent/plasticizer together with the composites. However, water is not considered a plasticizing agent/plasticizer in the present application since the function of absorbent products is to absorb water. Relying on water as a plasticizing agent/plasticizer will impair the function of the product. Other parameters that hinder the use of water as a plasticizing agent/plasticizer include potential microbial growth. Before using the superabsorbent polymer composite in an absorbent article, any water present from the synthesis is dried off (e.g. to constant weight in an oven).

Also provided is a method for making a superabsorbent polymer composite as described above. The method comprises the steps of:

g. providing cellulosic nanofibrils having a diameter equal to or less than 100 nm suspended in a solvent,
h. optionally, adding microfibers having a diameter greater than 100 nm but less than or equal to 100 μm suspended in a solvent,
i. adding one or more monomers;
j. adding a neutralizer,
k. adding a crosslinker,
l. adding an initiator, and
h. polymerizing the monomers and crosslinker to form a superabsorbent polymer composite including superabsorbent polymers, cellulosic nanofibrils and optionally microfibers.

Steps a), b), c), d), e) and f) can take place in any order.

The method of preparing the superabsorbent polymer composite may therefore involve adding one or more monomers (precursors to superabsorbent polymer) to a suspension of cellulosic nanofibrils, or vice-versa. Optionally, suspended microfibres having a diameter greater than 100 nm but less than or equal to 100 μm are added.

A neutralizer, a crosslinker and an initiator are added to the reaction mixture. Neutralizers and crosslinkers are described above. The method involves a crosslinker in order for the polymer chains and crosslinker to take the form of a three-dimensional network.

The polymerization usually requires an initiator to start and propagate the reaction. Any common polymerization initiators and/or polymerization catalysts known in the art may be used. Oxidizing initiators (e.g. peroxides or persulphates) and azo initiators (e.g. 2,2'-azobis[2-(2-imidazolin-2-yl)propane] dihydrochloride (VA-044) may be used. Other initiators include thermal initiators and photo initiators.

The preferred solvent for the polymerization reaction is water. However, other solvents such as alcohols, ethers or amide solvents (e.g. DMF) may be used, alone or in combination with water. The polymerization reaction can take place at a temperature between −40° C. and 100° C., and the reaction temperature can be used to control the reaction rate (polymerization reactions are generally exothermic).

If the resultant superabsorbent polymer composite is to be used in an absorbent article, it should be dried.

The composite may be used in various forms, including gels, fibers, particles and foams. Particles or foams are particularly of relevance. Generally, one characteristic that is evident when the composite is in the form of foam or particles is the irregularity of the surface structure, thus creating a larger surface area.

Particles

The superabsorbent polymer composite as above can be in the form of particles.

The particles are suitably surface crosslinked. The performance of the composite particles can be improved by surface crosslinking in addition to the ordinary (bulk) crosslinking, thus creating a higher crosslinking density at the surface of the particles and consequently increasing the absorption properties of the particle. Suitable surface crosslinkers are for example metal salts; polyols such as glycerol, sorbitol, aklykene carbonate and quarternary ammonium compounds.

When the composite is in the form of particles, the nanofibrils may be completely incorporated within the particles.

The method described above for making the superabsorbent polymer composite may therefore further include the step of (i): forming the composite into particles. This step should take place after step (h) in the above method. The composite may be made into particles via gelling. Gelling of the superabsorbent polymer composite takes place by exposing the composite to an elevated temperature until gelling occurs, e.g. at least 10 minutes. The container containing the superabsorbent polymer composite gel is then closed, the heat source is turned off and the container is allowed to stand for some time. Thereafter the gel is washed in water for a period (e.g. three days) and the water is changed regularly (e.g. every day) to remove extractable material. Then the gels are dried until a constant weight is reached. Thereafter the dried gels are ground and sieved to form particles of a certain size. Other methods of drying the composites (e.g. freeze-drying) may be used prior to grinding and sieving the particles.

Foam

The superabsorbent polymer composite may also be in the form of a foam. A typical mean pore size of the foam composite is below 1000 μm.

Suitably, the foam includes one or more substances selected from the group consisting of plasticizers, surfactants and blowing agents. Any plasticizer mentioned above in relation to the superabsorbent polymer composite itself is suitable for use in the foam composite. Surfactants such as e.g. SDS or Tween 80 may be used. Blowing agents include compressed gases that expand when pressure is released, soluble solids that leave pores when leached out, liquids that develop cells when they change to gases, and chemical agents that decompose or react under the influence of heat to form a gas. Chemical blowing agents range from simple salts to complex nitrogen releasing agents. Examples of blowing agents/porogens are sodium bicarbonates and ammonium bicarbonates which produce carbon dioxide gas when submitted to acidic conditions. Other examples are isocyanate-groups which produce carbon dioxide when submitted to water or azo-groups which produce nitrogen gas when submitted to heat. Other possible components of the foam are viscosity control agents.

To make a foam, the method described above for making the superabsorbent polymer composite may be carried out, including the step of (g): forming the composite into a foam; wherein step (g) takes place after steps (a)-(f), but before step (h) of the above method. This step (g) should be carried out before the polymerizing step (h), as the polymerized mixture may be difficult to form into a foam.

The method for forming the foam may further include the steps of adding one or more substances selected from the group consisting of plasticizers, surfactants and blowing agents. Additionally, the method may further comprise the steps of adding a viscosity control agent.

In effect, the foams may be made by:
foaming the mixture of nanofibrils and/or microfibers, one or more monomers and optionally plasticizer, and
polymerizing the monomers and crosslinkers to form a foam composite inlcuding superabsorbent polymers, cellulosic nanofibrils and optionally microfibers.

Solid foams can be prepared by various methods, which are generally divided into two main steps; 1. Bubble initiation and growth and 2. Solidifying.

Bubble Initiation and Growth

Several options are possible for bubble initiation and growth, e.g.
a. Whipping gas into a liquid.
b. Injecting gas into a liquid.
c. Bubbles can also form spontaneously in a liquid when the vapor pressure of the gas becomes higher than the ambient pressure.
d. Nucleation of gas bubbles by either chemical methods or physical methods.

e. A two phase system could also be achieved in a solid/liquid system. The solid phase will then be removed after the solidifying process.

Chemical methods are often associated with using blowing agents or porogens. Blowing agents are additives which—as above—are able to evolve gas through well-defined chemical reactions and produce foam structure in polymeric materials. Although the terms "blowing agents" and "porogens" are often used to mean the same thing, porogens are sometimes defined as those blowing agents which do not decompose through well-defined chemical reactions, but that, at very high temperatures, fall randomly apart in all kinds of molecular fragments.

Bubbles could also be produced by emulsions and microemulsions which include changing physical conditions to ensure a cellular structure. Examples are making emulsions or microemulsions with hydrocarbons with a low vaporization temperature (for instance heptane or acetone). Supercritical fluids, like supercritical carbon dioxide could also be used to produce a cellular structure.

In the bubble initiation and growth phase there are several components that could be used to facilitate this process. Examples are surface active components, so called surfactants. Proteins could also be used as surface active materials. Some particulates or fibres could also be used as nucleation sites for bubbles. The cellular structure could be stabilized using a viscosity control agent in the liquid phase, or in the air-liquid interface.

Solidifying Process

A solid foam is produced in the solidifying process which often is a polymerization of monomers in the liquid phase. The polymerization could be by a radical mechanism. Step-growth polymerization is also plausible. The polymerization temperature could be ambient or over or below room-temperature. Polymerization which takes place in a two phase system, in which water, at temperatures below its freezing point is one of the phases, produces so-called cryogels. When water is removed, a foam is produced.

It is also plausible that the solidifying process could occur by a physical change of the liquid phase for instance gelation and/or drying.

The method of making a foam of the superabsorbent polymer composite may include the step of extracting the water with 99.95% ethanol. The most preferred method for forming foams is by whipping.

Foam with Pore Gradient

Figure 3:
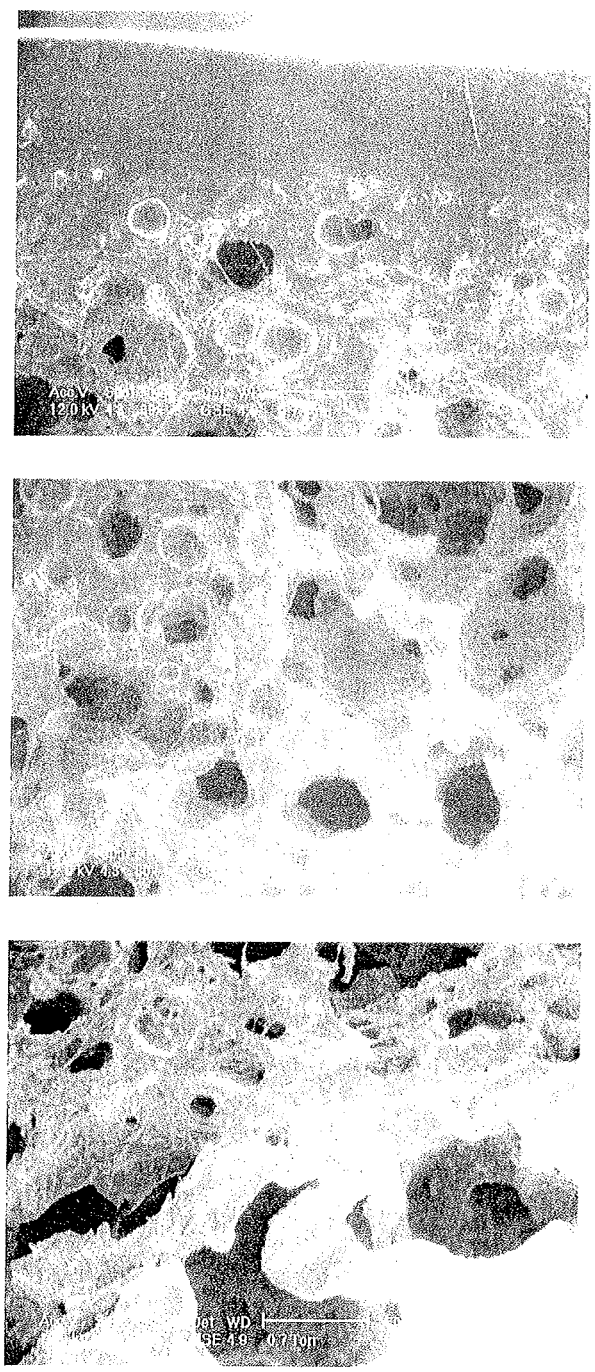
FIG. 3 shows an ESEM picture wherein the pore gradient of sample F2 is visible. The scale lines in FIG. 3 correspond to 500 µm.

By controlling the nature of the bubble initiation and growth process it is possible to produce cellular structures with different pore sizes, pore structures and/or pore gradients. Therefore, the foam may have a pore size gradient, see FIG. 3. The foam can include different pore sizes and pore gradients in different regions thereof.

The pore gradient can be in the z-direction with largest pores in the upper part leading to smaller and smaller pores as the lower part is reached. One advantage of using such a structure in absorbent articles is that the upper part of the absorbent structure located closest to the wearer can be provided with a higher liquid distributing capacity than the lower liquid storage portion of the absorbent structure. Furthermore, the lower part of the foam has a higher capillary pressure and thereby empties the upper part, allowing further wetting and giving a dry upper surface.

In order to obtain such a pore size gradient, different layers of foam are manufactured and placed on top of each other. By applying the different layers on top of each other before they are dry, an integrated structure will be obtained, where the layers partly penetrate into each other. One advantage of such an integrated structure—as compared to an absorbent structure including separate layers—is that a subsequent joining step is thus eliminated. Such a structure is thus cheaper to manufacture since the need for an adhesive and/or energy supply for joining the layers is eliminated. Another advantage with an integrated structure is that the function of the structure is improved in such a way that the liquid transport does not risk deterioration at the transition from a first layer to a second layer due to insufficient contact between the layers.

Figure 4A:
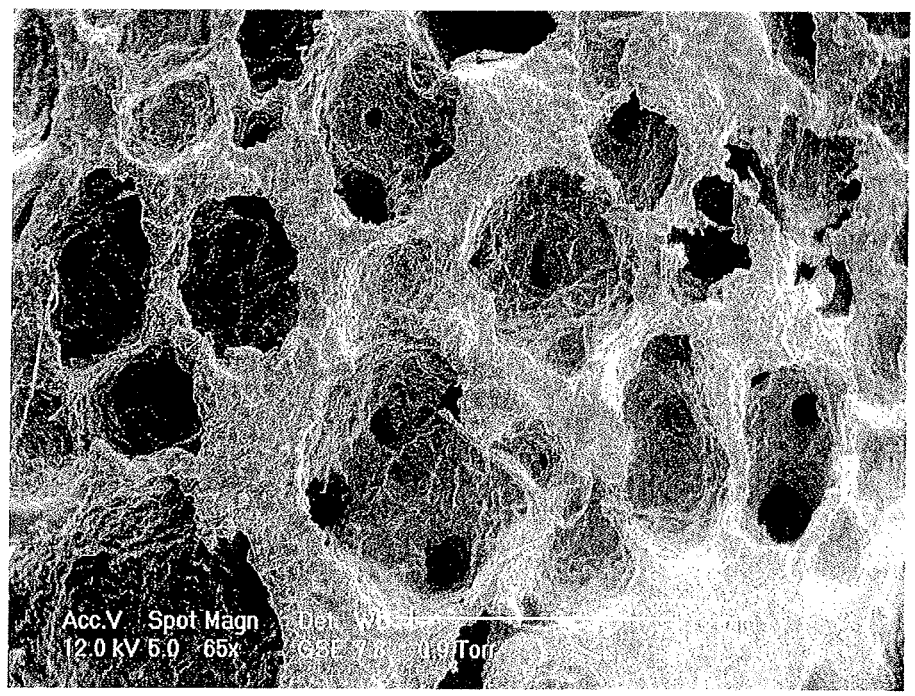
FIG. 4A shows an ESEM picture of an open cell composite foam (sample F3). The scale line in FIG. 4A corresponds to 1 mm.
Figure 4B:
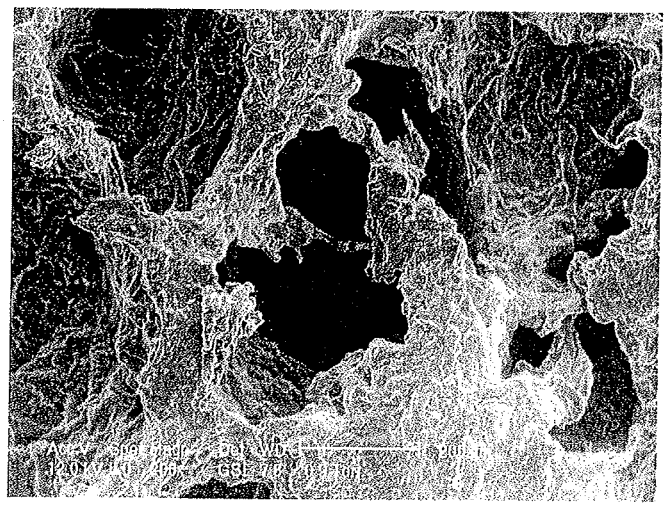
FIG. 4B shows an ESEM picture and a schematic picture of a cell wall containing nanofibrils and microfibres (sample F3). The scale line in FIG. 4B corresponds to 200 µm.

When the composite is in the form of a foam, the nanofibrils may be completely incorporated within the pore walls of the composite, see FIGS. 4A and 4B. This phenomenon occurs mainly due to the small size of the nanofibrils. The nanofibrils can be seen lying parallel to each other as well as entangled within the pore walls of the composite. They may be evenly distributed or gathered in several separated groups. Shorter and longer nanofibrils are distributed throughout the composite.

By incorporating nanofibrils, the ability of the foam composite to withstand both tensile and shearing stresses is improved. Further the foam is more easily compressed, i.e. it can be compressed to higher densities and yet expand when wetted, without exhibiting much of the brittleness associated with the foams of the prior art.

Absorbent Article

The superabsorbent polymer composite can be advantageously used in absorbent articles, due to its beneficial absorbing, storage and gel strength properties. In such an embodiment, an absorbent article has an absorbent structure including the superabsorbent polymer composite disclosed herein.

The absorbent article may be a feminine product, such as sanitary napkins and pantyliners, as well as baby diapers and incontinence guards. In other words, the absorbent article can be a diaper, a pant diaper, an incontinence guard, a sanitary napkin or the like and of the kind including a liquid pervious topsheet, a liquid impervious backsheet and said absorbent structure arranged therebetween. Most suitably, the absorbent structure includes the superabsorbent polymer composite. The absorbent structure may further include additional material such as fibrous material, e.g. cellulose fibers, tissue layers or non-woven materials in combination with the superabsorbent polymer composite.

The absorbent structure in the liquid acquisition portion (where liquid initially contacts the absorbent structure) may be more crosslinked than the liquid storage portion (where liquid is ultimately stored). A very highly crosslinked superabsorbent material can not receive so much liquid as a superabsorbent material having a lower degree of crosslinking. A superabsorbent material with a high degree of crosslinking has lower risk for gelblocking. Such an absorbent structure may be made by preparing two or more composite layers, in which a higher amount of crosslinking agent is added to the polymer solution which is going to form the liquid acquisition layer and a smaller amount of crosslinking agent is added to the polymers solution that is going to form the liquid acquisition portion. After forming of particles or foam and crosslinking, but before drying, the different layers are placed on top of each other, at which the layers will partly integrate with each other and a continuous structure is achieved.

One advantage of the superabsorbent polymer composites is that the amount of nanofibrils in the polymer composite can be varied, instead of varying the degree of crosslinker. As shown in the appended Examples, the gel strength of the superabsorbent polymer composites can be varied by varying the amount of nanofibrils and microfibers, without greatly affecting the absorption capacity. The maximum swelling is affected by the amount of NFC and MFC added to the composite, in the same way as adding a crosslinker, but with the advantage that the gels become less brittle (see Table 1 below).

An absorbent article e.g. diaper, pantyliner, incontinence guard, sanitary napkin or the like can include the superabsorbent polymer composite in the form of particles or foam as set out above. In particular, the absorbent structure of the absorbent article may include the superabsorbent polymer composite in the form of a foam, in which the foam has a pore gradient, as described above. The foam is placed with the largest pores in the upper part (i.e. closest to the wearer) leading to smaller and smaller pores as the lower part is reached (i.e. furthest from the wearer).

The absorbent structure of an absorbent article may also include particles of the superabsorbent polymer composite, arranged in layers such that particles nearer the wearer-facing surface of the structure are larger than those nearer the garment-facing surface thereof.

Also provided is a method for making an absorbent structure. The method includes making the superabsorbent polymer composite as above, suitably in the form of a foam or particles, and incorporating the resulting superabsorbent polymer composite into said absorbent structure.

Also provided is the use of cellulosic nanofibrils for increasing the gel strength of a superabsorbent polymer. All details regarding the superabsorbent polymer and the cellulosic nanofibrils given above are also relevant to this aspect.

The present invention should not be considered as limited by the above embodiments and the Figures, but rather the scope of protection should be determined by the enclosed claims. Combinations of features and elements as described for various embodiments above should also fall within the scope of the invention.

EXAMPLES

Two studies were carried out.

In the first study (Section I) nanofibrils and microfibers were prepared (Section I-a). Superabsorbent polymer composites in the form of particles and foams were formed (Section I-b and I-c), the composites were characterized (Section I-d), the liquid absorbency properties of the foams were tested (Section I-e) and the mechanical properties of the foams were tested (Section I-f).

In the second study (Section II), suspensions containing a mixture of nanofibrillated cellulose (NFC) and microfibrillated cellulose (MFC) were characterized (Section II-a), hydrogels were synthesized (Section II-b) and mechanical measurements and swelling analyses were carried out (Section II-c).

Section I
I-a. Preparation of Nanofibrils and Microfibres
Preparation of Nanofibrils One way of preparing nanofibrils is described in WO2009/069641. Cellolusic pulp/fibers are suspended in water and 2,2,6,6-tetramethylpiperidine-1-oxyl (TEMPO) and NaBr are added. By adding 12% NaClO solution with pH 10 to the cellulosic fiber suspension during stirring at 500 rpm, TEMPO-oxidation is initiated. The pH is maintained at 10 by adding NaOH during stirring. The TEMO-oxidized cellulose is washed with water by filtration and stored at 4° C. before further treatment. The oxidized cellulose is agitated using a magnetic stirrer bar at 1500 rpm in an airtight container for 6 h to 10 days at 4° C. As a result, individual nanofibrils and/or clusters of nanofibrils are prepared.

Preparation of Microfibers

Mircrofibers can be produced by different mechanical and chemical treatments. The microfibers used in the following examples were produced at SCA's CMC mill Nyhamn, Sweden. These fibers had a degree of substitution of 0.28 and were sold under the trade name AQUASORB. The carboxymethylated fibers were dispersed in distilled water to a concentration of 5%. The dispersion was kept over night in order to fully swell the fibers. It was then mechanically treated in a Hobart mixer, model N50, at maximum intensity for 2 h. The dispersion was then treated in an ultrasonic bath; model Elma transonic 700, for 30 min.

Samples
Sample S1: 0 wt % nanofibrils, reference (high crosslinking degree)
Sample S2: 12 wt % nanofibrils to wt acrylic acid monomer (low crosslinking degree)
Sample S3: 0 wt % nanofibrils to wt acrylic acid monomer, reference (low crosslinking degree)
Sample F1: 14.6 wt % microfibre to wt acrylic acid monomer
Sample F2: 2.16 wt % nanofibril and 6.6 wt % microfibre to wt acrylic acid onomer
Sample F3: 5.1 wt % nanofibril and 5 wt % microfibre to wt acrylic acid monomer Preparation of the Samples—Superabsorbent Polymer Composite Particles and Foams Based on Polyacrylic Acid Cellulose Microfibres and Manofibrils.

Raw Material

All chemicals were used as received. All syntheses were performed with Ultra Pure Elga water (resistivity=18 M$\Omega$), Elga Maxima HPLC. Acrylic acid monomer (AA), Tween 80 and NaOH were purchased from Merck. NN'-methylenbis (acrylamide) (MBA) and 2,2'-azobis[2-(2-imidazolin-2-yl) propane]dihydrochloride (VA-044) and Sodium dodecyl sulfate (SDS) were purchased from Sigma-Aldrich. Cellulose fibers as a 5% microfiber solution and as a 1.5% nanofibril solution in deionized water were used.

I-b. Synthesis of SAP Particles

All samples were prepared in glass vials with an inner diameter of 29 mm. The pure SAP and SAP containing nanofibrils were synthesized via a thermally-initiated free radical polymerization, MBA was used as the cross-linker and VA-044 was used as the initiator.

The content of the reaction vessel was purged with $N_2$ during all steps in the following examples to exclude oxygen from the solution. The $N_2$ source was removed before addition of the initiator.

Example 1

Sample S1: 0 wt % Nanofibrils, Reference (High Crosslinking Degree)

A cooling bath (cold water+ice) was placed on a magnetic stirrer. 5.24 g NaOH (67% neutralization of the acid groups) was dissolved in 17.009 g Ultra Pure Elga water. A vial was charged with 13.255 g Ultra Pure Elga water, 13.8 g acrylic acid monomer (0.192 mol) and placed in the cooling bath. After 10 minutes of mixing, the NaOH solution was added to the vial drop by drop. The vial was placed in a water bath preset to 42° C. and 0.242 g crosslinker MBA (0.85 mol % to mol monomer) was added; the stirring speed was raised to ensure incorporation of the powder onto the solution. After 10 minutes the initiator VA-044 (0.1 mol % to monomer, 0.059 g) was added with a syringe as a 10% solution in Ultra Pure Elga water. The temperature of the bath was raised to 50° C. and the reaction was allowed to proceed at 50° C. 10 minutes after formation of the network the vial was sealed, the heat source was turned off and the vial was allowed to cool and stand in the water bath overnight at 22° C.; a rubbery gel was obtained.

Example 2

Sample S2: 12 wt % Nanofibrils to wt Acrylic Acid Monomer (Low Crosslinking Degree)

To increase the nanofibril concentration of the solution, a certain amount of nanofibril solution (1.5% in deionised deionized water) was filtered to remove a part of water. The nanofibrils were still wet and contained water after this step. An E-flask was charged with 17.863 g nanofibril solution (0.62 g nanofibrils) and then the flask was introduced in a cold water bath. 3.705 g NaOH (67% neutralization of the acid groups) was added in small increments to the E-flask and the solution was mixed well until all NaOH pellets were dissolved.

A cooling bath (cold water+ice) was placed on a magnetic stirrer. The nanofibril-NaOH solution was transferred to a vial, then 19.5 g nanofibril solution (0.60 g nanofibrils) was added and the vial was placed in the cooling bath. Mixing of the solution was performed for ca 15 min, thereafter 10 g acrylic acid monomer (0.139 mol) was added to the vial drop by drop. Then 0.089 g crosslinker MBA (0.42 mol % to mol monomer) was added to the vial and the stirring speed was raised to ensure incorporation of the powder onto the solution. The vial was placed in a water bath preset to 42° C. After 10 minutes the vial was sealed and the initiator VA-044 (0.1 mol % to mol monomer, 0.047 g) was added with a syringe as a 10% solution in Ultra Pure Elga water. The vial was turned up and down a couple of times and shacked shook to mix the solution well, the temperature of the bath was raised to 50° C. and the reaction was allowed to proceed at 50° C. 10 minutes after formation of network, the heat source was turned off and the vial was allowed to cool and stand in the waterbath over night at 22° C. A rubbery gel was obtained. Total amount nanofibrils=1.2 g (12 wt % to wt monomer)

Example 3

Sample S3: 0 wt % Nanofibrils, Reference (Low Crosslinking Degree)

A cooling bath (cold water+ice) was placed on a magnetic stirrer. A vial was charged with 25.53 g Ultra Pure Elga water, 10 g acrylic acid monomer (0.139 mol) and placed in the cooling bath. 14.98 g NaOH solution (as 25% solution in Ultra Pure Elga water, 67% neutralization of the acid groups) was added to the vial drop by drop.

The vial was placed in a water bath preset to 42° C. and 0.089 g crosslinker MBA (0.42 mol % to mol monomer) was added to the vial; the stirring speed was raised to ensure incorporation of the powder onto the solution. After 10 minutes the initiator VA-044 (0.1 mol % to mol monomer, 0.045 g) was added with a syringe as a 10% solution in Ultra Pure Elga water. The temperature of the bath was raised to 50° C. and the reaction was allowed to proceed at 50° C. 10 minutes after formation of network the vial was sealed, the heat source was turned off and the vial was allowed to cool and stand in the water bath over night at 22° C. A rubbery gel was obtained.

I-c. Preparation of SAP Foams

The SAP foams were prepared via a thermally-initiated free radical polymerization, MBA was used as the crosslinker and VA-044 was used as the initiator.

Example 4

Sample F1: 14.6 wt % Microfiber to wt Acrylic Acid Monomer $N_2$ gas was used as the inert gas during all steps. A hand blender type Bosch MSM6600 (2008) was used for mixing and whipping of the mixture. The whipping speed of the blender has two positions; one defined as turbo speed and one for lower speed. The lid of the reaction vessel had one inlet for $CO_2$ gas, one for $N_2$ and addition of solutions and one for the balloon whip. The reaction vessel was placed in a cooling bath (cold water+ice) and purged with $N_2$ gas a couple of minutes. The vessel was charged with 37.04 g microfiber solution (5% in deionized water, 1.85 g microfibers) and the blender was started at low speed. 7.3 g NaOH (51.7% neutralization of the acid groups) was added in small increments to the vessel and the solution was mixed until all NaOH pellets were dissolved. 19.05 g acrylic acid monomer was added to the mixture drop by drop in two increments. After the first addition, 3.4 g surfactant (SDS) was added and after a mixing time of 2 minutes the addition of the acrylic acid was continued.

0.1976 g crosslinker MBA (0.36 mol % to the total mol monomer) was dissolved in 6.35 g acrylic acid monomer. The solution was added to the vessel in two increments. Whipping was performed at turbo speed for 15 minutes and thereafter the initiator VA-044 (0.13 g, 0.11 mol % to mol monomer) was added as a 3.8 wt % solution in Ultra Pure Elga water; mixing at lower speed was performed for 5 minutes. Thereafter, 37.04 g microfiber solution (5% in deionized water, 1.85 g microfibers) was added and whipping was continued for 5 minutes; a monomer foam structure was obtained. The reaction vessel was removed from the cooling bath and the monomer foam was carefully transferred to a rectangular plastic jar (10×10 cm). A lid was used to close the jar and the polymerization was performed in a heating oven at a temperature of 55° C. for 1½ hours. Then the lid was opened but not removed from the jar and the reaction was allowed to proceed over night at a temperature of 30° C.

Example 5

Sample F2: 2.16 wt % Nanofibril and 6.6 wt % Microfiber to wt Acrylic Acid Monomer $N_2$ gas was used as the inert gas during all steps. A hand blender type Bosch MSM6600 (2008) was used for mixing and whipping of the mixture. The whipping speed of the blender has two positions one defined as turbo speed and one for lower speed. The lid of the reaction vessel had one inlet for $CO_2$ gas, one for $N_2$ and addition of solutions and one for the balloon whip.

An E-flask was charged with 36.095 g nanofibril solution (1.5% in deionized water, 0.541 g nanofibrils) and 7.3 g NaOH (51.7% neutralization of the acid groups) was added in small increments to the E-flask; mechanical stirring was performed until all NaOH pellets were dissolved.

The reaction vessel was placed in a cooling bath (cold water+ice) and purged with $N_2$ gas a couple of minutes. The vessel was charged with 16.8 g acrylic acid monomer and the nanofibril-NaOH solution was added drop by drop; a magnetic stirrer was used for mixing of the solution. Thereafter the bar magnet was removed and the balloon whip was used for mixing and whipping. 3.3 g surfactant, SDS, was added to the mixture and after a couple of minutes MBA-acrylic acid monomer solution, 0.198 g MBA (0.4 mol % to total mol acrylic acid monomer)/8.2 g acrylic acid, was added in two increments. Whipping was performed at turbo speed for 10 minutes and thereafter 15.04 g microfiber solution (5% in deionized water, 0.752 g fibers) was added. After 5 minutes whipping, the initiator VA-044 (0.125 g. 0.11 mol % to mol monomer) was added as a 3.8 wt % solution in Ultra Pure Elga water and mixing at lower speed was performed for 5 minutes. Then 18.0 g microfiber solution (5% in deionized water, 0.9 g microfibers) was added and whipping was continued for 5 minutes at turbo speed. The vessel was removed from the cooling bath and the monomer foam was carefully transferred to a rectangular plastic jar (10×10 cm). A lid was used to close the jar and the polymerization was performed in a heating oven at a temperature of 65° C. for 1 hour. Thereafter, the lid was open but not removed from the jar and the reaction was allowed to proceed 4 hours at a temperature of 65° C.

Example 6

Sample F3: 5.1 wt % Nanofibril and 5 wt % Microfiber to wt Acrylic Acid Monomer

Both $CO_2$ and $N_2$ were used in this synthesis. $CO_2$ was used as a physical foaming agent and was inlet at the bottom of the reaction mixture to allow gas flow into the mixture from below while $N_2$ was used to avoid gas escape from the top of the mixture during the foaming process.

To be able to increase the amount of nanofibrils without increasing of the amount water, a certain amount of nanofibril solution (1.5% in deionized water) was filtered. For this aim an E-flask, a funnel and filter paper was used. The nanofibrils were still wet and contained water after filtration. For efficient mixing/whipping of the mixture, a reaction vessel just large enough to allow free rotation of the balloon whip was used in this example. The lid of the reaction vessel had one inlet for $CO_2$ gas, one for $N_2$ and addition of solutions and one for the balloon whip. The balloon whip was permanently fixed on a metallic bar which could be attached directly to an electrical motor.

An E-flask was charged with 25.354 g nanofibril solution (0.683 g nanofibrils) and 9.07 g NaOH (65.3% neutralization of the acid groups) was added in small increments to the E-flask; magnetic stirring was performed until all NaOH pellets were dissolved. The E-flask was introduced in a cooling bath and 16.25 g acrylic acid monomer was added drop by drop.

The reaction vessel was placed in a cooling bath (cold water+ice) and purged with $CO_2$ gas (6 B) a couple of minutes to exclude the air. The vessel was charged with 19.05 g nanofibril solution (0.594 g nanofibrils) and 0.25 g PEG 200 (1 wt % to total amount acrylic acid monomer). Mixing was performed at 300 rpm for 3 minutes and then the nanofibril-NaOH solution was added. At this step the $N_2$ gas was also introduced into the system but just on the surface of the mixture. Thereafter MBA-acrylic acid monomer solution, 0.196 g MBA (0.4 mol % to total mol acrylic acid monomer)/8.8 g acrylic acid, was added in two increments. Then 2.25 g surfactant, Tween 80, was added and the speed of the motor was raised to 500 rpm for 15 minutes; then 25.01 g microfiber solution (5% in deionized water, 1.25 g microfibers) and 0.66 g Tween 80 were added and whipping was continued for 5 minutes at 500 rpm. The initiator VA-044 (0.127 g, 0.11 mol % to mol acrylic acid monomer) was added as a 3.8 wt % solution in Ultra Pure Elga water and mixing at 240 rpm was performed for 3 minutes. The monomer foam was carefully transferred to a rectangular plastic jar (20×12 cm). The vessel was covered with a lid (not closed) and the polymerization was performed in a heating oven at a temperature of 65° C. for 2 hour.

Total nanofibril amount 2.527 (10 wt % to wt monomer).

I-d. Characterisation of the Superabsorbent Polymer Composites

Measurement of Nanofibril and Microfibre Diameter

Freeze-dried samples were used when measuring the diameter of the nanofibrils and the microfibers. The freeze dried samples were charaterized using a FEI Quanta 200 environmental scanning electron microscope (ESEM) equipped with a field emission gun (FEG). Small pieces of the samples were cut with a scalpel and put on a piece of carbon tape on a standard aluminium stub. The ESEM was operated at an acceleration voltage of 10 kV and at a pressure of 0.98 torr in the low vacuum mode in order to avoid charging effects during imaging. The diameter of the nanofibrils and microfibers were measured from images acquired at a magnification of 40,000× or higher.

The ESEM picture was then used to estimate the nanofibril and microfiber diameter. The procedure was as follows:

Open image with Optimas 6.51

Calibration spatial to get the active calibration

Visual measuring of nanofibrils and microfibers

Optimas 6.51 software was obtained from PARAMETER Box 27186, 102 52 Stockholm. One should note that our image is a combination of individual nanofibrils/microfibers and/or clusters of nanofibrils/microfibers.

An ESEM image has been used. To improve the estimation of the diameter one can use an atomic force microscope (AFM). The AFM or scanning force microscope (SFM) is a very high-resolution type of scanning probe microscope, with demonstrated resolution of fractions of a nanometer.

Characterization of the Morphology of SAP Particles and SAP Foam

The surface and cross section morphology of the prepared materials were studied with Environmental Scanning Electron Microscopy, Philips ESEM XL-30 TPM.

I-e. Measurements of Absorption Properties

An aqueous solution of 0.9% NaCl and defibrinated sheep blood were used as test liquids. The defibrinated sheep blood was purchased from the National Veterinary Institute (Statens Veterinarmedicinska Anstalt, 751 89 Uppsala, Sweden).

Prior to measuring absorption properties, gels were washed in deionized water for three days and the water was changed every day to remove extractable materials. Then the samples were dried in a heating oven at 40° C. until a constant weight was reached. Thereafter the samples were ground and sieved to cover the common size interval used for hygiene absorbent articles 140-850 μm.

Absorption Under Load (AUL) in an Aqueous Solution of 0.9% NaCl.

The test was performed according to the standard test WSP 242.2 (05), Gravimetric determination of absorption under pressure. A glass filter plate is placed in a Petri dish and NaCl solution is added until the surface of the liquid reaches the same level as the surface of the glass filter. A filter paper of same dimension as the glass filter was placed on it and was allowed to be totally wetted.

0.9 g SAP particles of size 140-850 μm are distributed onto the filter screen of a Plexiglas cylinder. The Plexiglas piston is placed in the cylinder and the complete assemble is weighed. The cylinder assemble is placed on the filter paper and at the same time the weight (2.5 kPa) was placed into the piston. After 60 minutes the cylinder assembly is lifted from the filter paper, the weight is removed and the cylinder assembly is reweighed.

In this test some of the samples were analyzed after 60 minutes.

The AUL per gram dry polyacrylic acid was calculated according to the equation:

$$AUL = \frac{(m_w - m_d)}{m_s} \quad \text{Eqn. 1}$$

where:
$m_w$=weight of cylinder assembly with sample after absorption
$m_d$=weight of cylinder assembly with dry sample
$m_S$=weight of dry sample Each of the results presented below are mean values of three measurements.

The following table indicates AUL values (gram absorbed liquid per gram dry polyacrylic acid) of particles measured in an aqueous solution of 0.9% NaCl.

| Sample | abs (after 60 min) |
|---|---|
| S1 | 20.6 |
| S2 | 19.7 |
| S3 | 9.4 |

Sample S2 shows a slightly lower AUL value measured in an aqueous solution of 0.9% NaCl than sample S1 and a substantially higher value than sample S3. The presence of nanofibrils in sample S2 increases the AUL value compared to sample S3. The presence of nanofibrils in sample S2 may compensate for the lower crosslinking degree compared to sample S1 in terms of AUL.

2. Absorption Under Load (AUL) in Defibrinated Sheep Blood

A crystallization bowl (75 mm inner diameter) is charged with 40 ml defibrinated sheep blood. 0.15 g SAP particles of size 140-850 μm are distributed onto the filter screen of a Plexiglas cylinder (25 mm inner diameter). The weight (2 kPa) is placed into the cylinder, the whole assemble is weighed and placed on a perforated metallic cylinder holder and then immersed into the sheep blood. After 20 minutes of absorption, the apparatus is lifted from the blood and allowed to drop for 10 minutes; then the assembler is reweighed.

The AUL per gram dry polyacrylic acid was calculated according to Eqn. 1. Each of the results presented below are mean values of three measurements.

The following table indicates AUL values (gram absorbed liquid per gram dry polyacrylic acid) of particles measured in defibrinated sheep blood.

| Sample | abs (after 20 min) |
|---|---|
| S1 | 4.0 |
| S2 | 8.0 |
| S3 | 5.0 |

As can be seen sample S2 indicates the highest AUL value measured in defibrinated sheep blood compared to sample S1 and S3. The presence of nanofibrils gives sample S2 the most advantageous absorption under load value regardless of crosslinking degree.

I-f. Measurements of Mechanical Properties

Swelling of Dry Foam Samples for Determination of Mechanical Strength of the Foams The dry samples were weighed. Then the dry weight of the samples was multiplied with the same factor to get samples with the same swelling degree.

Example $M_{dry\,foam}$=0.230 g $V_{H2O}$=0.230*71=16.33 g

The dry sample was placed in a small vessel, 16.33 g deionized water was added and the vessel was covered to avoid evaporation of liquid. The sample was allowed at room temperature for 8 hours and then subjected to uniaxial mechanical compression analysis. All samples were swelled to 71 times the dry weight. The cross-sectional area of each swelled sample was measured as 22.1±0.9 cm².

The mechanical properties of the foams in the swollen states have been evaluated with a Lloyd LRX tensile tester. The tensile tester is connected to a computer equipped with Ondio V4.0 software for automatic control of the machine, programming of test set-ups and to record the load-deformation curve (load, extension/compression).

The probe was comprised of one fixed Plexiglas plate and one mobile Plexiglas plate, each having a surface area of 19.7 cm². The compression test was carried out with a load cell (50 N; 101.1% accuracy) at 23±1° C. and R.H. 50±10%. The measurement was carried out at a constant crosshead speed of 50 mm/min.

The swollen foam was carefully positioned between the parallel Plexiglas plates of the instrument. A preload force of 0.05 N was used for auto-measurement of the initial high of the swollen foams and 50% compression of the sample's initial high was performed at the constant crosshead speed. The compression was monitored as force (N) vs. extension.

The following values of force at 50% compression of the initial height of the swollen foam were found. All samples were swelled to a water content of 71 times the dry weight of the sample.

| Test | Sample | load after 50% compression (N) |
|---|---|---|
| 1 | F3 | 22.4 |
| 2 | F2 | 2.3 |
| 3 | F1 | 1.8 |

Sample F3 shows the highest load after compression values compared to the other foam samples. Thus, the higher content of nanofibrils in the sample the higher values of load after 50% compression.

Section II

II-a. Characterization of a Suspension of Nanofibrillated (NFC) and Microfibrillated (MFC) Cellulose Materials The following chemicals were of analytical grade and were used as received: acrylic acid [AA] (Fluka, Belgium), N,N'-methylenebisacrylamide [MBA] (Sigma-Aldrich, Germany), sodium chloride (Sigma-Aldrich, Germany), sodium hydroxide (Sigma-Aldrich, Germany), potassium persulfate [KPS] (Sigma-Aldrich, Germany). Suspensions of Nanofibrillated cellulose [NFC] and microfibrillated cellulose (MFC) was bought from the Paper and Fibre Research Institute PFI, Norway. Used $H_2O$ was of Milli-Q grade.

Both untreated and filtered NFC+MFC suspension was characterized using light microscope and AFM. Filtered suspension was further characterized by transmittance analysis.

Filtered suspension of NFC and MFC was prepared using a 25 mm syringe filter with 0.2 µm nylon membrane (VWR), previously washed with 30 ml of $H_2O$.

For the light microscopy analysis an Olympus BH2 research microscope with a Microscope digital camera system DP12 (Olympus) was used in transmission mode. For untreated NFC+MFC suspension, images were recorded for concentrations of 0.03 and 0.8% w/v, placed between a standard microscope glass slide and a cover slip. For filtered suspension images were recorded on samples dried at room temperature on a standard microscopy glass slide, utilizing filtered and dried $H_2O$ as controls.

Untreated NFC+MFC suspension, samples to be analyzed in AFM were prepared by diluting the suspension to fiber concentrations of 0.16, 0.016 and 0.0016% w/v. For both untreated and filtered NFC+MFC one drop of sample was added to a freshly cleaved mica chip and was allowed to dry at room temperature; for the filtered sample filtered water was used as control. The AFM analysis was performed using a Digital Instrument Nanoscope IIIa with a type G scanner (Digital Instrument Inc.). The cantilever used was a Mikro Masch silicon cantilever NSC 15. The AFM was operated at a resonance frequency of about 330 kHz in tapping mode, the scan rate was 1 Hz and the measurements were performed in air.

For transmittance analysis of filtered NFC+MFC suspension the extinction of light passed through the sample in a quartz cuvette was recorded as a function of wavelength in the interval 200-800 nm using a Cintra 40 spectrophotometer (GBC), filtered $H_2O$ was used as a control.

During the visual inspection of the untreated suspension it was noted that small amounts of fibrous structures could be detected with the naked eye and that the suspension appeared opaque. The filtered suspension appeared completely transparent.

Optical microscopy of wet suspension of NFC and MFC revealed a highly heterogenous suspension on the detectable length scale, as can be seen in the exemplifying images in FIG. 1a. Filtered and subsequently dried suspension of NFC and MFC left a film-like aggregate over the whole area covered by the drop prior to drying. In the aggregate area, structures of varying size could be seen, many with clear directionality and even fractal like structures. It was found that extent, size and shape of the structures varied between samples. This was probably due to different concentrations and size distributions of MFC and NFC in the samples after filtration and due to variations in drying between samples. Exemplifying images can be seen in FIG. 1b. The controls with filtered water did not show any observable structures and only negligible aggregate, probably being an artifact from the filtration or the drying. The large aggregate formation and the formed structures from NFC+MFC suspension filtered through a 0.2 µm filter clearly indicates the presence of structures with sizes on the nano-scale.

AFM analysis of the wet suspension of NFC and MFC revealed that they contained a large amount of nanoparticles, thought to be cellulose nanocrystals, as well as larger fibers and fibrous structures. An exemplifying image showing individual nanoparticles, fibers and larger fibrous structures is given in FIG. 2a. Typical dimensions in the z-direction were found to be about 2-5 nm for nanoparticles and individual fibers and about 30-60 nm for fiber bundles. However, the structure observed varies greatly between location and preparation procedure, as such there will be structures present falling outside the mentioned intervals. The observed nanoparticles had diameters in the xy-plane of 10's of nanometers; this being similar to diameters reported by others for spherical cellulose nanocrystals. The exact diameters of the nanoparticles are not speculated upon. This since the AFM tip is known to give artifacts in the xy-plane. However, the AFM has very high precision in the z-direction, and it can be concluded that the structure of the presumed cellulose nanocrystals is somewhat flattened.

Figure 2:
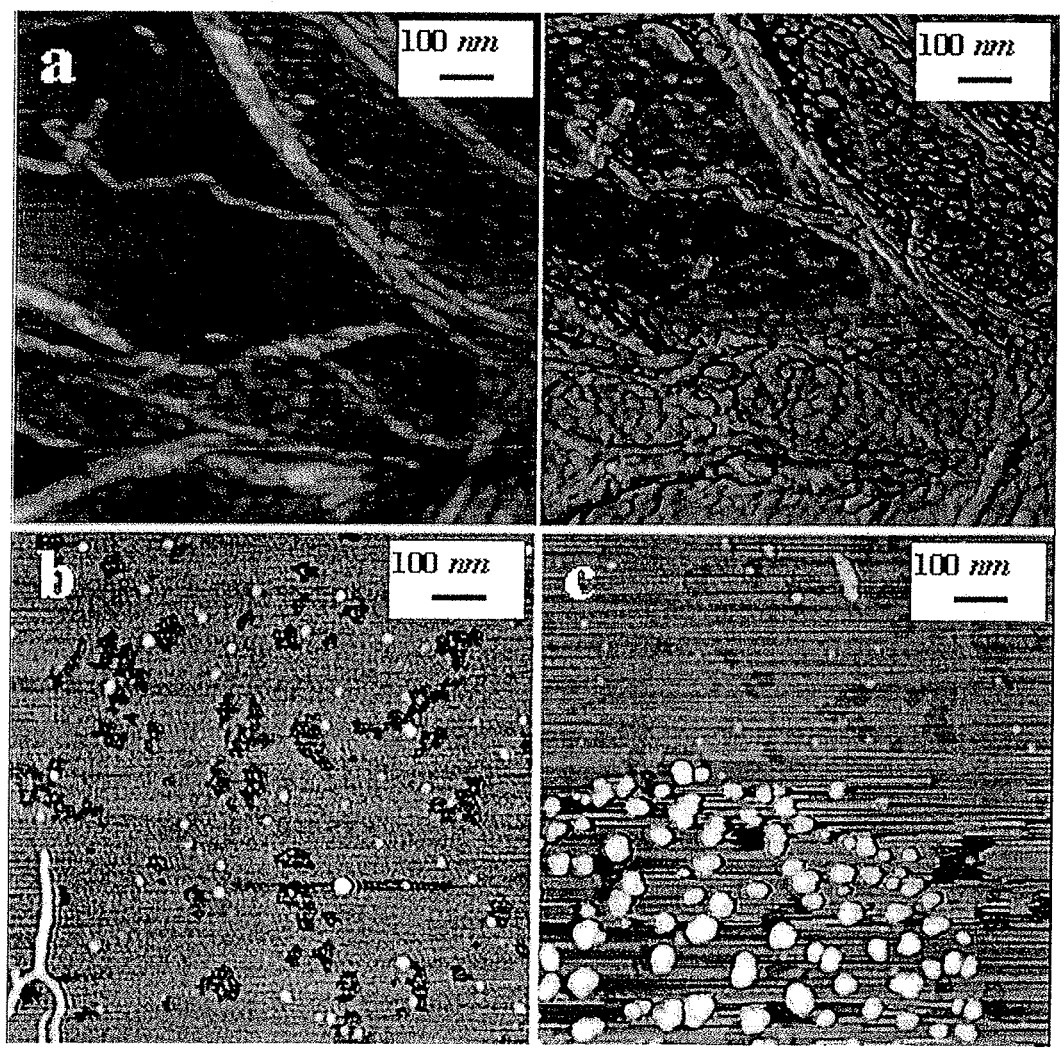
FIG. 2 shows AFM images of a suspension of nanofibirillated (NFC) and microfibrillated (MFC) cellulose. (a) 10× diluted and subsequently dried, recorded in an area where no macroscopic aggregate was observed using light microscope. z-displacement (range 20 nm) to the left, phase image to the right. (b) and (c) z-displacement images (range 30 nm) of filtered and subsequently dried nanofibirillated cellulose. The images have been digitally enhanced for clarity. All scale lines in FIG. 2 correspond to 100 nm.

AFM analysis of the filtered suspension of NFC and MFC and the filtered water control revealed that the filtered suspension of NFC and MFC contained nanoparticles and fibers (FIGS. 2b and c). The dimensions in the z-direction ranged from about 1-20 nm for the nanoparticles and 1-2 nm for the fibers. As stated earlier, structures falling outside the mentioned intervals could also be present. The AFM analysis of the water control revealed that a thin film with pores had been formed upon drying of the sample (result not shown). Thus, the dark areas corresponding to cavities in FIGS. 2b and c are derived from this film, and are not an effect of the filtered suspension.

The transmittance analysis of the filtered suspension showed an increasing extinction with decreasing wavelength. The transmittance through a medium containing particles can be described by the Beer Lambert law, replacing the extinction coefficient with a scattering coefficient, with the current notation:

$$A = \alpha_{sca} l \quad (3)$$

where A is the absorbance, l is the distance through the medium and $\alpha_{sca}$ is the scattering coefficient, which for Rayleigh scattering from small size particles is inversely proportional to the fourth power of the wavelength.

Taking into account the results from optical microscopy of filtered suspension, AFM and transmittance studies, it is concluded that the suspension of NFC and MFC contains a rather large amount of structures having sizes on the nano scale. The differences in the structures observed in the AFM analysis of the 10, 100 and 1000 times diluted samples, as well as the structures observed for filtered and dried NFC+MFC using optical microscopy, indicates that upon drying, the nanoparticles aggregate into larger structures in a concentration-dependent manner. Based on the characterization it is recognized that the NFC/MFC mixture is highly heterogenous, containing structures ranging from nanometers to hundreds of micrometers.

II-b. Synthesis of Hydrogels

Hydrogels containing 25% w/v AA with degree of crosslinking ranging from 0 to 5 mol % relative to AA and concentrations of MFC+NFC ranging from 0 to 0.75% w/v were synthesized by free radical copolymerization as follows: AA was drop wise neutralized to 60 mol % with NaOH. The neutralized AA was mixed with MBA, KPS, $H_2O$ and NFC suspension (1.6% w/v). KPS was used in a concentration of 21 mM, the amounts of MBA and NFC+MFC suspension were added according to desired final concentrations and $H_2O$ was added to reach the final volume. All of the mixing was performed on ice during stirring. After mixing the samples were bubbled with $N_2$ gas under stirring while kept on ice for 30 minutes, this to remove $O_2$ from the samples. The samples were then immediately transferred to 7×40 mm autosampler vials (NTK KEMI), which were placed in a water bath at 70° C. for 6 h for the synthesis solution to polymerize. Finally the samples were allowed to settle over night at room temperature before breakage of the vials and further analysis.

II-c. Mechanical Measurements and Swelling Analysis

In order to evaluate the effect of the NFC+MFC on the mechanical and swelling properties of the hydrogels, a series of samples were studied. To evaluate the effect of the amount of NFC+MFC on the properties in a fixed surrounding matrix, this series of samples contained hydrogels with a crosslinking degree of 0.5 mol % N,N'-methylenebisacrylamide (MBA) crosslinker relative to acrylic acid (AA) and NFC+MFC concentrations ranging from 0 to 2.5% per dry weight of the samples.

Equilibrium Swelling and Elastic Modulus

In order to establish the effect of NFC+MFC on equilibrium swollen gels the samples were submerged in 0.9% NaCl solution. The specified ionic strength was chosen because of the biological relevance and because superabsorbents swollen in deionized water commonly fracture during swelling.

Figure 5:
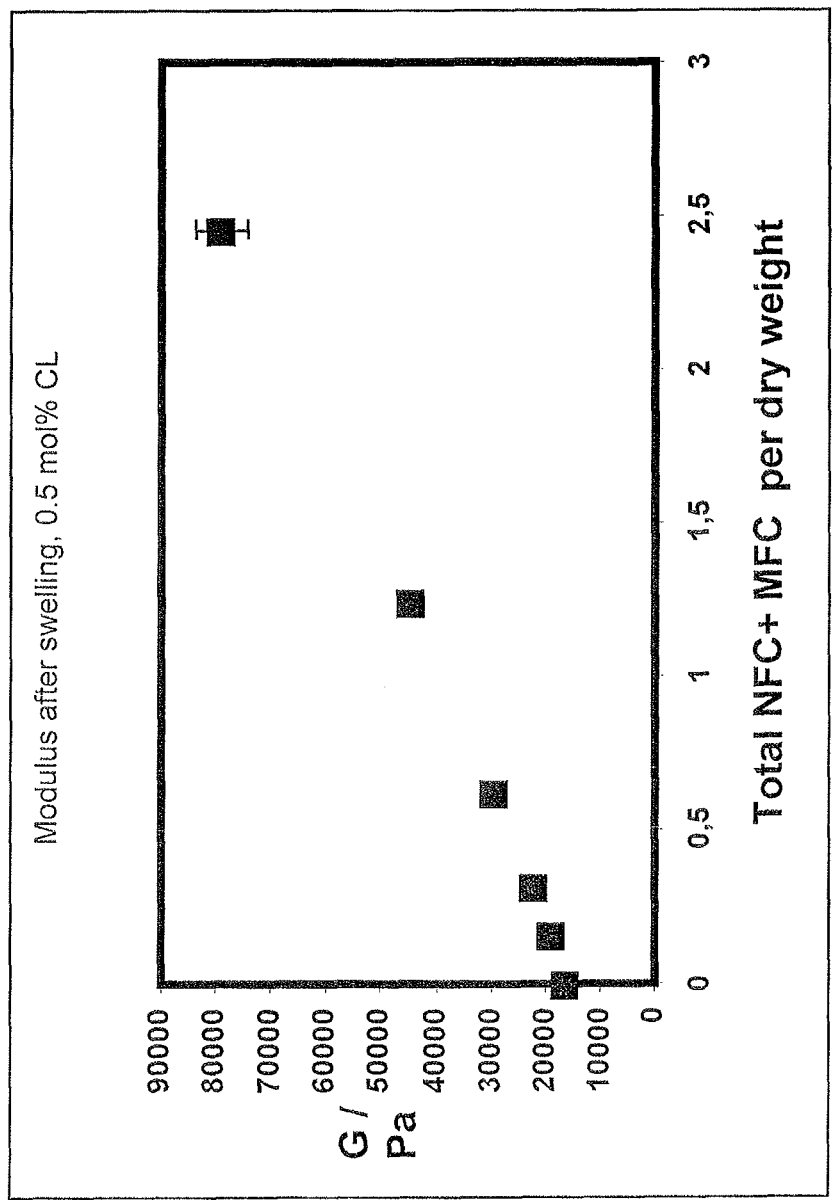
FIG. 5 shows how the Elastic Modulus, G, ($G=P/(\alpha-\alpha^{-2})$) after swelling of a composite containing 0.5 mol % cross-linker (CL), varies according to the total amount of NFC and MFC (per dry weight %) in said composite.

The swelling studies revealed, that the equilibrium swelling decreased with increasing total content of NFC+MFC (FIG. 5).

Figure 6:
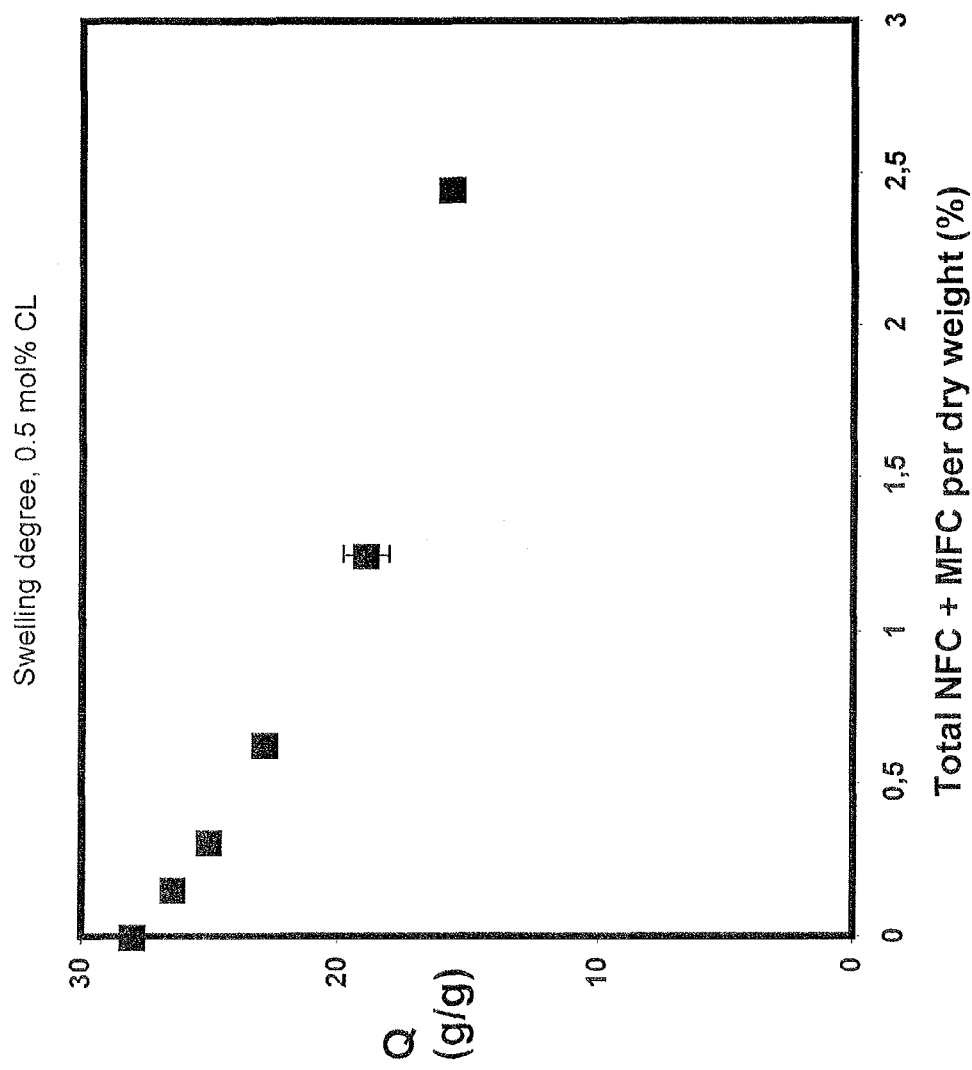
FIG. 6 shows the swelling degree (Q in g/g) for a composite containing 0.5 mol % cross-linker in relation to the total amount of NFC and MFC per dry weight %.

The elastic modulus after swelling of the samples displayed an increase with increasing mass of NFC+MFC, shown in FIG. 6.

Studies also showed that, for samples containing NFC+MFC, the stress at fracture (compressive strength) $\sigma_f$ was increased without decreasing the strain at fracture, compared to corresponding samples without NFC+MFC (see Table 1 below).

Mechanical Measurements

The gels were cut into cylinders intending an aspect ratio>1.5. However, on rare occasions a smaller aspect ratio was acquired due to removal of rough sample ends. Uniaxial compression tests were performed in order to determine the elastic modulus G of the different samples. The samples were compressed at 0.1 mm·s$^{-1}$ and the resulting force was recorded using a TA-HDi® (a texture analyzer sold by Stable Microsystems), with a load cell capacity of 5 kg. The compression probe used was a 25 mm cylindrical aluminium probe (Stable Microsystems). Measurements were performed at 20±0.5° C. For the uniaxial compression of Gaussian chains the following equation is valid:

$$P = G(\alpha - \alpha^{-2}) \quad (5)$$

where P is the pressure, G is the elastic modulus and a is the ratio deformed length to initial length.

For deformation ratios up to 20% the elastic modulus was determined as the slope of the linear region in the graph P versus ($\alpha - \alpha^{-2}$). The non linear data for low strains was discarded as it is derived from imperfect geometries of the sample ends.

The compressive strength of the samples was calculated as:

$$\sigma = F/A \quad (6)$$

where F is the force at fracture and A is the area at fracture, calculated based on the assumption of constant volume as:

$$A = \frac{A_0}{\alpha_f} \quad (7)$$

where $A_0$ is the initial area and $\alpha_f$ is the deformation ratio at fracture.

Data for the fracture properties of gels after synthesis and after equilibrium swelling are given in Table 1.

TABLE 1

Fracture properties of gels after synthesis and after equilibrium swelling. $\epsilon_f$ denotes the strain at fracture, $\sigma_f$ the compressive strength and G the elastic modulus of the gels. ± indicates min/max values for samples after synthesis (n = 2) and one standard deviation for samples after equilibrium swelling (n = 6).

| Sample | MBA (mol %) | NFC + MFC (mass %) | $\epsilon_f$ | $\sigma_f$/kPa | G/kPa |
|---|---|---|---|---|---|
| After synthesis | | | | | |
| 1 | 5 | 0 | 0.37 ± 0.011 | 298 ± 5.0 | 249 ± 3.9 |
| 2 | 2.5 | 0 | 0.454 ± 0.0091 | 180 ± 17 | 120 ± 10 |
| 3 | 5 | 1.2 | 0.377 ± 0.0031 | 409 ± 7.0 | 301 ± 7.6 |
| 4 | 2.5 | 1.2 | 0.54 ± 0.047 | 440 ± 78 | 159.1 ± 0.71 |
| After Swelling | | | | | |
| 1 | 5 | 0 | 0.21 ± 0.023 | 190 ± 52 | 400 ± 27 |
| 2 | 2.5 | 0 | 0.34 ± 0.040 | 170 ± 35 | 166 ± 6.1 |
| 3 | 5 | 1.2 | 0.24 ± 0.034 | 340 ± 55 | 550 ± 20 |
| 4 | 2.5 | 1.2 | 0.32 ± 0.022 | 220 ± 36 | 247 ± 5.8 |

Swelling Analysis

The samples were prepared for swelling by cutting off and discarding the uppermost part of the cylinders and recording their weights $w_0$. The swelling experiments were conducted in 900 ml of 0.90% w/v NaCl at 20±0.5° C. After one week the samples were considered to have reached equilibrium swelling, as no further mass uptake could be detected. The equilibrium weight $w_{eq}$ was recorded. Assuming a yield of 100% from the synthesis, as done by others, the dry weights of the samples were calculated from the masses of the components in the synthesis mixture and the weight ratio between the initial weight $w_0$ of the samples and the synthesis mixture, so that:

$$m_{dry} = m_{AA} + m_{NaA} + m_{MBA} + m_{MFC} \quad (8)$$

where $m_{dry}$ is the theoretical dry weight of the sample, $m_{AA}$ is the mass of AA, $m_{NaA}$ is the mass sodium acrylate, $m_{MBA}$ is the mass MBA and $M_{NFC}$ is the mass of cellulose fibrils (NFC+MFC) in the sample. The swelling degree Q was then calculated as:

$$Q = \frac{(w_{eq} - m_{dry})}{m_{dry}}$$

The invention claimed is:

1. A superabsorbent polymer composite comprising cellulosic nanofibrils having a diameter equal to or less than 100 nm incorporated within a three-dimensional network of polymer chains of a superabsorbent polymer.

2. The superabsorbent polymer composite according to claim 1, wherein the composite does not contain cellulosic fibers having an average diameter greater than 100 μm.

3. The superabsorbent polymer composite according to claim 1, wherein the superabsorbent polymer comprises CMC (carboxymethyl cellulose) or a repeating unit derived from the group consisting of acrylic acid and its salts, methacrylic acids and its salts, and combinations thereof.

4. The superabsorbent polymer composite according to claim 1, further comprising an organic cross-linker.

5. The superabsorbent polymer composite according to claim 4, wherein the superabsorbent polymer composite has an organic cross-linker content of 0.1-20 wt % compared to the amount of superabsorbent monomer in the composite.

6. The superabsorbent polymer composite according to claim 5, wherein the organic cross-linker content is 0.5-15 wt % compared to the amount of superabsorbent monomer in the composite.

7. The superabsorbent polymer composite according to claim 6, wherein the organic cross-linker content is 0.5-5 wt % compared to the amount of superabsorbent monomer in the composite.

8. The superabsorbent polymer composite according to claim 1, wherein the composite has a nanofibril content of 0.1-20 wt % compared to the amount of superabsorbent monomer in the composite.

9. The superabsorbent polymer composite according to claim 8, wherein the nanofibril content is 0.5-15 wt % compared to the amount of superabsorbent monomer in the composite.

10. The superabsorbent polymer composite according to claim 9, wherein the nanofibril content is 0.5-5 wt % compared to the amount of superabsorbent monomer in the composite.

11. The superabsorbent polymer composite according to claim 1, further comprising cellulosic microfibers having a diameter greater than 100 nm but less than or equal to 100 μm.

12. The superabsorbent polymer composite according to claim 11, wherein the cellulosic microfibers have a diameter greater than 100 nm but less than or equal to 10 μm.

13. The superabsorbent polymer composite according to claim 11, wherein the composite has a microfiber content of 0.1-20 wt % compared to the amount of superabsorbent monomer in the composite.

14. The superabsorbent polymer composite according to claim 13, wherein the microfiber content is 0.5-15 wt % compared to the amount of superabsorbent monomer in the composite.

15. A superabsorbent polymer composite particle comprising the superabsorbent polymer composite according to claim 1.

16. A superabsorbent polymer composite foam comprising the superabsorbent polymer composite according to claim 1.

17. The superabsorbent polymer composite foam according to claim 16, wherein the nanofibrils are incorporated into the pore walls of the foam.

18. The superabsorbent polymer composite foam according to claim 16, wherein the foam has a pore size gradient.

19. The superabsorbent polymer composite foam according to claim 16, wherein the foam comprises one or more substances selected from the group consisting of plasticizers, surfactants, and blowing agents.

20. An absorbent article having an absorbent structure comprising the superabsorbent polymer composite of claim 1.

21. The absorbent article according to claim 20, wherein said absorbent article is a diaper, a pant diaper, an incontinence guard, or a sanitary napkin and of the kind comprising a liquid pervious topsheet, a liquid impervious backsheet and said absorbent structure arranged therebetween.

22. A method for making a superabsorbent polymer composite according to claim 1, said method comprising the steps of:
   a. providing cellulosic nanofibrils having a diameter equal to or less than 100 nm suspended in a solvent,
   b. optionally, adding microfibers having a diameter greater than 100 nm but less than or equal to 100 μm suspended in a solvent,
   c. adding one or more monomers
   d. adding a neutralizer,
   e. adding a crosslinker,
   f. adding an initiator, and
   h. polymerizing the monomers and crosslinker to form a superabsorbent polymer composite comprising superabsorbent polymers, cellulosic nanofibrils and optionally microfibers,
wherein the steps (a), (b), (c), (d), (e) and (f) can take place in any order.

23. The method according to claim 22, wherein the initiator is at least one selected from the group consisting of oxidizing initiators, azo initiators, photoinitiators, and thermal initiators.

24. The method according to claim 22, further comprising the step of (g) forming the mixture of one or more monomers with at least one of nanofibrils or microfibers into a foam; after steps (a)-(f), but before step (h).

25. The method for making an absorbent structure, said method comprising carrying out the method of claim 22, and incorporating the resulting superabsorbent polymer composite, foam or particles into said absorbent structure.

26. The method according to claim 22, further comprising the step of (i) forming the composite into particles.

27. The method according to claim 26, further comprising the steps of adding one or more substances selected from the group consisting of plasticizers, surfactants, and blowing agents.

28. The method according to claim 26, further comprising the steps of adding a viscosity control agent.

* * * * *